United States Patent
Bernhardt et al.

(10) Patent No.: US 6,399,356 B1
(45) Date of Patent: Jun. 4, 2002

(54) PROCESS AND AGENT FOR SANITATION OF CONTAMINATIONS CAUSED BY VIRUSES

(75) Inventors: Dieter Bernhardt, Cöibe; Albrecht Gröner, Seeheim, both of (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 09/364,050

(22) Filed: Jul. 30, 1999

(30) Foreign Application Priority Data

Jul. 29, 1998 (DE) .......................... 198 34 053

(51) Int. Cl.⁷ ................................ C12N 7/06

(52) U.S. Cl. .................... 435/238; 435/236; 435/235.1

(58) Field of Search ................... 435/236, 238, 435/235.1

(56) References Cited

U.S. PATENT DOCUMENTS

| 4,333,941 A | * | 6/1982 | Baratz et al. |
| 4,998,984 A | | 3/1991 | McClendon et al. |
| 5,094,960 A | * | 3/1992 | Bonomo |
| 5,162,037 A | * | 11/1992 | Whitson-Fischman |
| 5,801,153 A | * | 9/1998 | Badaway |

FOREIGN PATENT DOCUMENTS

| AU | 40323/95 | 6/1996 |
| DE | 31 17 792 | 11/1982 |
| DE | 38 29 200 | 3/1990 |
| DE | 195 23 320 | 1/1997 |
| EP | 0 720 851 | 7/1996 |
| JP | 05 306217 | 11/1993 |
| WO | 91 13626 | 9/1991 |

OTHER PUBLICATIONS

JP 05306217, Patent abstracts of Japan, vol. 18, No. 114 (C–1171), Feb. 24, 1994.
Aruoma, O.I., et al., An Evalution of the Antioxidant and Antiviral Action of Extracts of Rosemary and Provencal Herbs, Food & Chemical Toxicology, Chemical Abstract No. 97:9438, 1996.
Crance, J.M. et al., Inhibition of Hepatitis A Virus Replication in Vitro by Antiviral Compounds, Chemical Abstract No. 113:144908, 1990.
Bourne, K.A., et al., Plant products as topical microbicide candidates: assessment of in vitro and in vivo activity against herpes simplex virus type 2, Chemical Abstract No. 131:252125, 1999.
Derwent Abstract 90–361964/49, Plant hygiene disinfectant composition contains naturally occuring phenol compound aromatic and wetting agent, Sterling Drug Inc., Mar. 16, 1989.
European Search Report for Appln. No. 99114405.6–2110, Nov. 25, 1999.

* cited by examiner

*Primary Examiner*—Leon B. Lankford, Jr.
(74) *Attorney, Agent, or Firm*—Finnegan, Henderson, Farabow, Garrett and Dunner, L.L.P.

(57) ABSTRACT

A process and an agent for the sanitization of tissues or cell cultures and also of materials and equipment which can be contaminated with viruses are described. For sanitization, a solution of a substituted phenol or of a substituted phenol ether is employed here which as substituents carries one or two saturated or unsaturated hydrocarbon radicals which in each case can have up to 4 carbon atoms.

8 Claims, No Drawings

PROCESS AND AGENT FOR SANITATION OF CONTAMINATIONS CAUSED BY VIRUSES

The invention relates to a process and an agent for the sanitization of contamination caused by viruses in cell cultures or tissues and of materials and equipment which can be contaminated with viruses. This contamination can be known (studies in virology) or unknown (studies with, for example, noninfected cell cultures or with tissue/organ explants from healthy humans or animals).

It is known that when working with human pathogenic viruses such as HIV, HBV or HCV, serious diseases such as AIDS or hepatitis can occur in the case of transfer to a sensitive recipient. This danger is particularly great in investigation and research laboratories in which work with human pathogenic viruses is carried out. In addition, the cell cultures available there can be an ideal nutrient medium for the replication of viruses and the viruses can be easily spread from one medium to another if it is not possible to reliably sanitize used materials and equipment again after virus contamination has taken place. During organ transplantation, viruses present in the organ can be transferred to the recipient of the transplant; on account of the avoidance of rejection reactions for immunosuppression of the recipient, which is customary and brought about medicinally, a virus infection which has taken place in this manner can lead to serious disorders. A particular type of organ transplantation is blood transfusion, which as is known can lead to the transfer of viruses.

In addition to physical sanitization processes, chemical sanitization processes have also already been proposed. A particularly frequently discussed chemical process is the SD (solvent/detergent) method. It is suitable for inactivating coated viruses, i.e. viruses which are surrounded by a lipid-containing membrane, but has the crucial disadvantage of being completely ineffective against all known uncoated viruses. For reasons of safety, there is therefore a great need to make available chemical sanitization processes which also reliably inactivate uncoated viruses.

In European patent application 0 720 851, a process for the inactivation of viruses with the aid of acridine or acridine derivatives, preferably in combination with benzalkonium chloride, has already been described, which can be carried out in the presence of proteins whose biological activity is not significantly impaired thereby. There is, however, furthermore a high need for agents which are able to eliminate contaminations caused by viruses selectively in tissues or cell cultures so that these can then be available again in a clean condition and can yield unadulterated investigation and research results. At the same time, there is a need for the sanitization of materials and equipment used in virology in order that no virus transfers from one medium to another can take place by means of them. Surprisingly, it has now been found that the differing requirements in the sanitization of a cell culture contaminated by viruses and the materials and equipment used in virology can be fulfilled by one and the same agent.

The invention relates to a process for the sanitization of contaminations caused by viruses in tissues or cell cultures, and of materials and equipment used in virology or in the production of biological materials, whose starting materials can be contaminated with viruses, in which for sanitization a solution of a substituted phenol or of a substituted phenol ether is used, which as substituents can carry one or two saturated or unsaturated hydrocarbon radicals which in each case can have up to 4 carbon atoms. The process mentioned can also be employed for the sanitization of organ transplants or in blood transfusions and plasma donations and other blood constituents or cellular blood components.

The substituted phenols or substituted phenol ethers employed in the process according to the invention have such a wide spectrum of action that they can be effectively employed not only against coated, but also against uncoated viruses. The phenolic compound employed here is preferably a compound from the group consisting of eugenol, isoeugenol, thymol, carvacrol, carvacrol methyl ether and menthol.

The phenolic compounds mentioned are dissolved in a suitable solvent, for example in a mixture of ethanol and water, in the ratio 1:10 to 10:1 and added to the contaminated cell culture in a total amount of less than 0.1% by weight, based on the contaminated substrate. The same solution, however, is also outstandingly suitable for sanitizing laboratory equipment contaminated with viruses, in particular chromatography columns and resins. In general, for the elimination of the virus contamination a solution is employed which contains the active compound in a concentration of 0.1 g/l to 0.001 g/l. The sanitization is preferably carried out at a temperature of 2 to 70° C. and at a pH of 5 to 9. A temperature range from 20 to 60° C. is very particularly preferred. In this temperature range, even after a time of action of only 10 minutes, the beginning of sanitization of the contaminated substrate can be detected. A satisfactory sanitization, however, usually requires a period of time of 2 to 6 hours, which only exceptionally has to be extended to up to 24 hours.

In general, it is not necessary to remove residual amounts of the substituted phenol or phenol ether after sanitization has been carried out. Should this be necessary, however, known methods are available for this, for example absorption on active carbon, dialysis or chromatographic processes.

A particular advantage of the process according to the invention for the sanitization of contaminations caused by viruses is the preservation to the greatest extent of the cell cultures or treated with it. The biological activities of the cell cultures or are not adversely affected thereby. The sanitization agent according to the invention has already exhibited its activity against retro-, toga-, flavi-, picorna-, herpes-, adeno-, reo-, influenza, parainfluenza, calici-, corona- or astroviruses.

The present invention is illustrated in greater detail by the following examples:

EXAMPLE 1
Sanitization of a DEAE-Sephadex Chromatography Column 1 g of DEAE-Sephadex A-50 (pre-swollen) was added as a slurry in 20 ml of PBS (pH 7.2) to 500 ml of a reo-3-virus-containing aqueous solution (cell culture supernatant with 5% FCS) having a virus titer ($CCID_{50}$) of 5.5 $log_{10}$. After stirring for 30 min at approximately 20° C., all the material was transferred to a chromatography column and, after sedimentation of the resin, the column was emptied. The resin was then washed with 150 ml of wash buffer (0.2 M NaCl, pH 6.0 by means of $KH_2PO_4$/NaOH) and finally eluted with elution buffer (2.0 M NaCl, pH 8.0 by means of $KH_2PO_4$/NaOH). For sanitization, the column was washed (in countercurrent) with 3 column volumes of a wash buffer containing carvacrol solution (1:2000) and allowed to stand overnight at approximately 20° C. under this carvacrol solution. The column was then regenerated with wash buffer. The virus titers of the various fractions are indicated in Table 1.

TABLE 1

Virus content of various fractions from chromatography

| Sample | Virus titer CCID$_{50}$/ml[log$_{10}$] | Virus load (Titer × volume) [log$_{10}$] |
|---|---|---|
| Virus-containing starting material (500 ml) | 5.5 | 8.2 |
| Flow (510 ml) | 5.2 | 7.9 |
| Wash buffer (150 ml) | 4.7 | 6.9 |
| Elution buffer (20 ml) | 5.0 | 6.3 |
| Carvacrol solution* [1st column volume] (12 ml) | 4.2 | 5.3 |
| Carvacrol solution [after about 16 hours' incubation] (12 ml) | ≦1.5 | ≦2.6 |
| Wash buffer after sanitation [2nd column volume] (12 ml) | ≦1.5 | ≦2.6 |

*Titer determination immediately after having obtained of the sample

As the example shows, after the elution of the DEAE-Sephadex chromatography column virus remains in the column; re-use of the column without sanitization led to a contamination of the subsequent product batch with virus. Sanitization with carvacrol leads to a complete inactivation of reo-3-virus below the detection limit. There is accordingly nothing to stop re-use of the column material.

EXAMPLE 2
Sanitization of a Cell Culture

The determination of the virus content of a sample is carried out by infection of cell cultures (indicator cell containing serial dilutions of the sample to be tested and detection of virus replication in the respective cell culture vessels by virus-specific cytopathic effect (CPE). When the indicator cell is contaminated with foreign viruses, replication and/or the expression of the CPE can be adversely affected such that too low a titer is found. The replication of a cytopathogenic BVDV strain can be strongly inhibited (interference) by the contamination of a cell culture, e.g. MDBK, with a noncytopathogenic strain of a pestivirus. The infection of the cell culture can be followed, inter alia, by the (fetal) calf serum necessary for cell culture.

An MDBK cell culture which is infected with a noncytopathogenic pestivirus strain is passaged as is customary (splitting rate 1:5; Eagles Minimal Essential Medium containing 5% FCS) and two cell culture flasks are prepared. One cell culture flask remains untreated, the second cell culture flask is treated with thymol (1:50,000). Both cell culture flasks are passaged weekly, the treatment of the cell culture being carried out for 3 passages. After one passage without treatment, cells from the respective cell culture flasks are inoculated into microtiter plates and a titration (end point dilution method) of a cytopathogenic BVDV strain (Denmark) is carried out on the respective indicator cells. The cytopathogenic effect is evaluated as an indication of virus replication and the virus titer is calculated (Spaerman-Kärber method; Table 2).

TABLE 2

Determination of the virus content in an untreated and treated (thymol) cell culture

| Cell Culture | Virus titer (CCID$_{50}$ml) [log$_{10}$] |
|---|---|
| Starting cell culture | 4.3 |
| After 3 passages untreated | 3.9 |
| After 3 passages, thymol-treated | 7.6 |

By treatment of the MDBK cell with thymol, the non-cytopathogenic pestivirus is inactivated such that the cell again has an optimal sensitivity for the cytopathogenic BVDV strain.

What is claimed is:

1. A sanitization process which comprises sanitizing contaminations caused by viruses in tissues or cell cultures, blood, plasma, constituents of blood or plasma, or materials or equipment used in virology with a solution of a phenol or a phenol ether, wherein the phenol or phenol ether is substituted with one or two saturated or unsaturated hydrocarbon radicals, which have up to 4 carbon atoms.

2. The process as claimed in claim 1, wherein the viruses are coated or uncoated.

3. The process as claimed in claim 1, wherein the solution of the phenol or the phenol ether contains said phenol or phenol ether in an amount of less than 0.1 percent by weight, based on the contaminated substrate.

4. The process as claimed in claim 1, wherein the sanitization is carried out at a temperature between 15 and 70° C. and at a pH between 5 and 9.

5. The process as claimed in claim 1, wherein the sanitization is carried out over a period of 10 minutes up to 24 hours.

6. The process as claimed in claim 1, further comprising removing the phenol or the phenol ether from the substrate after completion of the sanitization.

7. The process as claimed in claim 1, wherein the contaminations caused by viruses are in chromatography columns/resins.

8. The process as claimed in claim 1, wherein the contaminations caused by viruses are produced by retro-, toga-, flavi-, picorna-, herpes-, adeno-, reo-, influenza, parainfluenza, calici-, corona- or astroviruses.

* * * * *